United States Patent [19]

Berke et al.

[11] 4,454,133
[45] Jun. 12, 1984

[54] ANTIMICROBIAL COMPOUNDS

[75] Inventors: Philip A. Berke, Madison; William E. Rosen, Summit, both of N.J.

[73] Assignee: Sutton Laboratories, Inc., Chatham, N.J.

[21] Appl. No.: 308,994

[22] Filed: Oct. 6, 1981

[51] Int. Cl.$^3$ .................... A01N 43/40; A01N 43/50; A01N 35/00
[52] U.S. Cl. ................ 424/267; 424/273 R; 424/333
[58] Field of Search .................. 424/273 R, 267, 333

[56] References Cited
PUBLICATIONS

Chem. Abst. 91:194596w, 1979, Resin-Treatment or Crosslinking Agent for Glut. and 5,5 Dimethy.

*Primary Examiner*—Allen J. Robinson
*Assistant Examiner*—John W. Rollins
*Attorney, Agent, or Firm*—Bacon & Thomas

[57] ABSTRACT

Compounds formed by condensation reactions of glutaraldehyde with various nitrogen-containing compounds are disclosed. The compounds exhibit antimicrobial activity and are useful in a method of protecting products susceptible to microbial contamination.

9 Claims, No Drawings

ANTIMICROBIAL COMPOUNDS

BACKGROUND OF THE INVENTION

This invention is directed to the field of antimicrobial compounds, compositions of such compounds and methods of using such compounds and compositions to inhibit microbial contamination of substances.

Glutaraldehyde is known to possess germicidal activity but is characterized by disadvantageous properties including instability in solution, offensive odor, skin irritation and skin sensitization. In our co-pending U.S. patent application Ser. No. 177,136, filed Aug. 8, 1980, there is disclosed condensation products of glutaraldehyde and allantoin which exhibit anti-microbial activity without the problems associated with glutaraldehyde.

SUMMARY OF THE INVENTION

We have now discovered that other compounds formed by condensation reactions of glutaraldehyde with various nitrogen-containing compounds, specifically amides and imides, also exhibit anti-microbial activity without the problematic characteristics exhibited by glutaraldehyde. Because of these properties, the compounds are valuable additives for many substances which require protection against the adverse effects of microorganisms. In addition to being active against bacteria, the compounds also exhibit fungicidal and fungistatic activity, i.e., activity against yeasts and molds.

Accordingly, it is a general object of the invention to provide a method for inhibiting microbial contamination in substances by incorporating therein an effective amount of an anti-microbial agent which is formed by the condensation reaction between glutaraldehyde and various amides and imides.

DETAILED DESCRIPTION OF THE INVENTION

The primary structural formula for the condensation reaction of glutaraldehyde with nitrogen compounds is as follows:

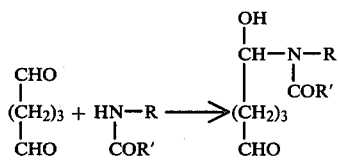

where the nitrogen compound is a linear or cyclic amide or imide, i.e., R and R' are hydrogen, alkyl, substituted alkyl, or amino, or R and R' together with the —NH—CO— to which they are attached form a cyclic amide or imide. When the nitrogen compound is a cyclic compound it will generally possess a five or six member ring with one or more nitrogen atoms as ring members.

Generally, one nitrogen atom in the nitrogen-containing compound can react with one aldehyde group in the glutaraldehyde molecule to form the grouping:

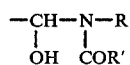

in some cases a nitrogen atom may be capable of reacting with two aldehyde groups as, for example, when R is hydrogen:

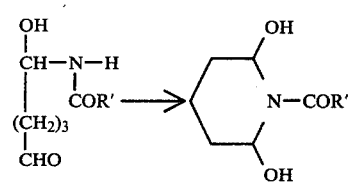

When the nitrogen-containing reactant contains more than one nitrogen, each nitrogen can react with an aldehyde group of the same or different glutaraldehyde molecule. Further, under certain conditions, the carbinolamine group,

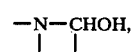

can dehydrate to form

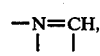

or polymerize to form repeating units

Thus, dimers and higher polymers can form by this route. Additionally, dimers, higher polymers and even new ring compounds can be formed by reaction of the aldehyde end groups of the glutaraldehyde molecule with nitrogens of the same or different nitrogen-containing reactant. Hence, it is possible to obtain reaction products in which the ratio of glutaraldehyde to nitrogen-containing reactant is 0.5:1, 1.5:1, 2.5:1, 3.5:1 and so forth, as well as whole number ratios.

Since one or both ends of the glutaraldehyde molecule can react with one or two nitrogens of the same or different nitrogen-containing reactant molecule, the number of possible reaction products is considerable. Moreover, when the end of a glutaraldehyde molecule condenses with the same nitrogen-containing molecule, both bonds of the terminal

group can be attached to the same or to two different nitrogen atoms. In the first case and when the nitrogen atom has two other groups attached to it, a positive charge arises at the nitrogen atom (e.g.,

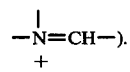

In general, base catalysis favors the production of the carbinolamine which is the preferred form of the reaction product. Acid catalysis and omission of catalyst favor dimer or polymer formation or dehydration of the carbinolamine to the Schiff base, —N=CH—. Because of the number of possible reactions, it is apparent that the term "condensation reaction" is used herein in the broad sense to include addition reactions, ring closure, and polymerization, as well as reactions in which water is eliminated.

Since the reaction products have both weakly acid and weakly basic amine groups, they can form salts with bases and acids. The alkali metal salts and the sulfates, nitrates, chlorides, and phosphates are illustrative. The present invention is intended to encompass all forms of the reaction products which exhibit anti-microbial activity.

In general then, the invention comprises a method for inhibiting microbial contamination of substances by incorporating therein an effective amount of an anti-microbial reaction product of glutaraldehyde and a linear or cyclic amide or imide not including allantoin. Because the product produced by the reaction of glutaraldehyde and allantoin is the subject of co-pending application Ser. No. 177,136 to the same inventors, this product is not being claimed in this application for patent.

The stabilities of the reaction products of the invention differ because stability is dependent upon the specific chemical structure of the nitrogen-containing reactant, which may be internally stabilized by hydrogen bonding. Generally, reaction products of imides are less stable in aqueous solution than products derived from amides. When the nitrogen-containing reactant contains two different functional nitrogens, such as in dimethylhydantoin which contains cyclic amide and imide groups, the amide nitrogen forms a more stable reaction product with glutaraldehyde than does the imide nitrogen. Thus, in aqueous solution, glutaraldehyde is released fairly rapidly from the imide nitrogen, but quite slowly from the amide nitrogen:

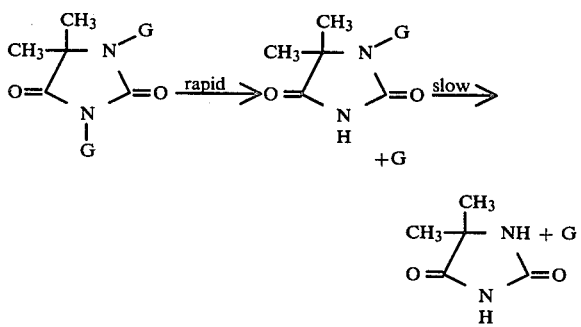

G = glutaraldehyde (—CH(OH)(CH$_2$)$_3$CHO).

It is, therefore, possible to produce a series of reaction products with varying degrees of anti-microbial activity based upon the rate of release of glutaraldehyde. It is also possible to obtain reaction products which exhibit anti-microbial activity without releasing glutaraldehyde.

The advantages of the anti-microbial reaction products of the invention over glutaraldehyde, are numerous. The reaction products are typically solids, which are easier to handle than glutaraldehyde solutions. Additionally, the reaction products are more stable than glutaraldehyde solutions alone, and when incorporated into substances as anti-microbial preservatives. Of further significance, the reaction products are typically less toxic than glutaraldehyde.

DESCRIPTION OF THE PREFERRED EMBODIMENTS

In its broadest sense, the invention encompasses any product formed by the reaction of glutaraldehyde and a linear or cyclic amide or imide (excluding allantoin) which exhibits anti-microbial activity. The amides or imides may be generally depicted as compounds having the structural formula:

where R and R' are either hydrogen, alkyl, chloroalkyl, or amino, or R and R' together with the NH—CO to which they are attached form a cyclic amide or imide.

The Tables below illustrate the numerous, diverse amides and imides which can be reacted with glutaraldehyde to form anti-microbial reaction products.

A. R and R'=H, alkyl or amino

| Substituents | Formula | Name |
|---|---|---|
| R = R' = H | HCONH$_2$ | formamide |
| R = CH$_3$, R' = H | HCONH—CH$_3$ | N—methylformamide |
| R = H, R' = CH$_3$ | CH$_3$CONH$_2$ | acetamide |
| R = R' = CH$_3$ | CH$_3$CONH—CH$_3$ | N—methylacetamide |
| R = H, R' = alkyl | CH$_3$(CH$_2$)$_n$CONH$_2$ | straight chain acid amides |
| R = H, R' = NH$_2$ | H$_2$NCONH$_2$ | urea |
| R = R' = NH$_2$ | H$_2$N—NH—CONH$_2$ | semicarbazide |
| R = H, R' = NH—X | H$_2$NCONH—X | urea derivative |

B. R and R'=linear or cyclic amide

1. R or R'=linear amide

| Substituents | Formula | Name |
|---|---|---|
| R = CONH$_2$, R' = H | H$_2$NCONHCHO | formylurea |
| R = CONH$_2$, R' = NH$_2$ | H$_2$NCONHCONH$_2$ | |
| R = H, R' = CONH$_2$ | H$_2$NCOCONH$_2$ | oxalic acid diamide |
| R = H, R' = CH$_2$CONH$_2$ | H$_2$NCOCH$_2$CONH$_2$ | malonic acid diamide |
| R = H, R' = (CH$_2$)$_n$ CONH$_2$ | H$_2$NCO(CH$_2$)$_n$CONH$_2$ | dicarboxylic acid diamide |

2. R and R' combine to form cyclic amide or imide

| Substituents | Formula | Name |
|---|---|---|
| R and R' = —CH$_2$CONH— | HN with cyclic structure (O=C, N-H, C=O) | hydantoin |
| R and R' = —C(CH$_3$)$_2$ CONH— | HN with cyclic structure, CH$_3$, CH$_3$ substituents | 5,5-dimethyl hydantoin |

-continued

| Substituents | Formula | Name |
|---|---|---|
| R and R' = <br> —CH—CH—NH— <br>     \|       \| <br>   NHCONH | [structure] | glycoluril |
| R and R' = <br> CH$_2$CH$_2$— <br> \| <br> CH$_2$— | [structure] | pyrrolid-2-one |
| R and R' = <br> CH=CH— <br> \| <br> CH$_2$— | [structure] | pyrazol-3-one |
| R and R' = <br> —CH=CHNH— | [structure] | imidazol-2-one |
| R and R' = <br> —C=C—NH— <br>  \|    <br>  CH    N <br>   \\ //<br>    N | [structure] | 8-hydroxy-purine |
| R and R' = <br> CO—CO— <br> \| <br> NH— | [structure] | parabanic acid |
| R and R' = <br> CO—CO— <br> \| <br> CO—NH— | [structure] | alloxan |

C. R and R' = H or chorolakyl

| Sustituents | Formula | Name |
|---|---|---|
| R = H, R' = ClCH$_2$ | ClCH$_2$CONH$_2$ | chloroacetamide |

Although any product formed by the reaction of glutaraldehyde and a linear or cyclic amide or imide (excluding allantoin) which exhibits anti-microbial activity is considered within the scope of the invention, regardless of whether or not it is specifically disclosed in the above Tables, several reaction products are considered preferred. These include the reaction product of glutaraldehyde and dimethylhydantoin, glycoluril and urea. Although the exact structural formalae for these products cannot be ascertained with certainty, the following formulae are consistent with observed nitrogen analysis:

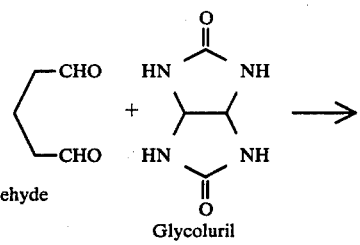

4 Glutaraldehyde + Glycoluril ⟶ (I)

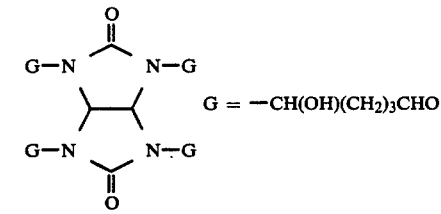

G = —CH(OH)(CH$_2$)$_3$CHO

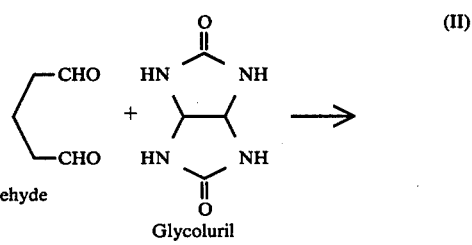

3 Glutaraldehyde + Glycoluril ⟶ (II)

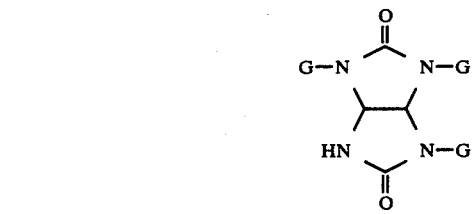

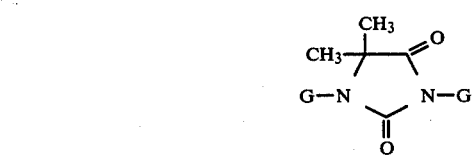

2 Glutaraldehyde + Dimethylhydantoin ⟶ (III)

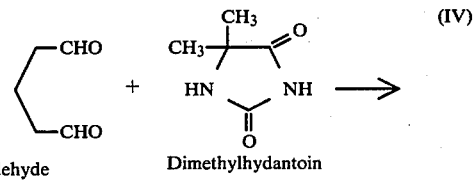

1 Glutaraldehyde + Dimethylhydantoin ⟶ (IV)

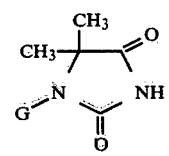

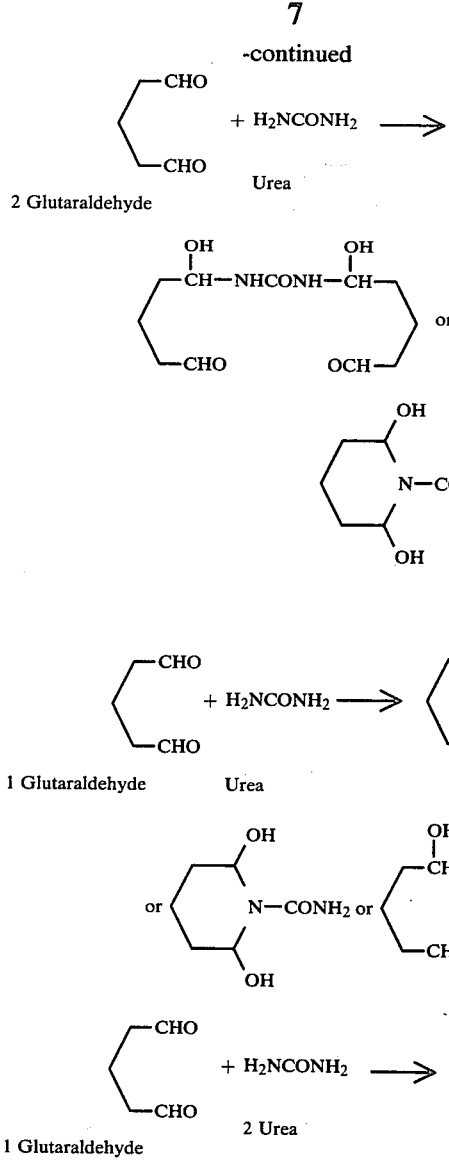

Other preferred products are formed by reaction of glutaraldehyde with formamide, acetamide and chloroacetamide.

The procedures used to prepare these exemplary products are described in Examples I—XII, infra. Of these exemplary products, those derived from glutaraldehyde and dimethylhydantoin in the ratio of glutaraldehyde to dimethylhydantoin of 1:1 and 2:1 are the most preferred.

These compounds and mixtures thereof as may exist in the reaction products, are useful as anti-microbial additives in substances for human, agricultural and industrial uses, in which an effective amount of the compound as an essential active ingredient, optionally combined with a suitable carrier, is added to the substance to be protected. The amount required will depend upon the particular anti-microbial reaction product selected and the particular use.

The reaction products, including their salts with acids and bases, can be used as valuable anti-microbial additives for any substance normally subject to spoilage by microorganisms selected from the group consisting of bacteria, yeasts and molds. They may be used as preservative agents in the fields of cosmetics, pharmaceuticals, foods, industrial products, and elsewhere where it is desired to add an anti-microbial agent. They may also be used for disinfectant and sterilizing purposes. Representative uses include, for example, use as additives in industrial products such as textiles, paints, glues, or cutting oils, embalming fluid, etc.; household products such as dishwashing compositions, floor wax emulsions, floor polishes, or laundry starches; cosmetic preparations such as hair preparations, lotions, or shampoos; foodstuffs such as fruits, vegetables, milk, eggs, meat, grains, cereal products; animal feeds and forage products; by-products or wastes that contain potentially valuable carbohydrates and/or proteins; as a disinfectant on surfaces such as floors, table tops, operating room walls and tables, etc.; as a sterilant for medical and dental instruments, equipment, etc.; and for sanitation purposes in cleaning compositions for restaurants, dairies, food plants, kennels, bird cages, slaughter houses, and the like. Other applications will readily suggest themselves to those employed in the relevant arts.

One mode of utilization of the products of this invention is by adding, as an essential active preservative ingredient, a minor but effective amount of glutaraldehyde-amide or imide reaction products to the compositions to be protected. The latter then become the carrier for the active anti-microbial agent. Since the compounds are generally water soluble, they can be added to cleaning and sanitizing solutions, or they can be added in the form of dry powders as the essential active anti-microbial agent to powdered compositions which are intended either to be used dry or to be dissolved prior to use. Similarly, in the case of cosmetic creams or lotions, the products of the invention can be added during the production process and emulsified into the cosmetic composition which then serves as the carrier for the active anti-microbial agent.

In all of the instances mentioned above only by way of illustration, the effective amount will vary with the intended use. Generally, for preservation purposes, about 0.5% or less by weight, based upon the weight of the material to be protected, will be effective. Solutions of higher concentration may be required for disinfectant or sterilizing purposes and in embalming fluids, e.g., 3% by weight or higher. However, it is entirely within the skill of the art for one working in any given field to readily determine by simple tests the most desirable proportions which would constitute an effective amount.

Without being limited thereby, the following examples illustrate the production of several representative novel compounds in accordance with the present invention.

EXAMPLE I

Product from 4 glutaraldehyde: 1 glycoluril

A mixture of 14.2 g. (0.1 mole) of glycoluril and 80.0 g. (0.4 mole) of 50% aqueous glutaraldehyde in 500 ml of water was stirred and adjusted to pH 8 by addition of approximately 1.5 ml of 10% aqueous sodium hydroxide. The white slurry was heated at 60±5° C. for 40 minutes, giving a clear colorless solution of the reaction product. Removal of water at reduced pressure left a white powder having Anal. Found: N, 10.55%.

EXAMPLE II

Product from 3 glutaraldehyde: 1 glycoluril

A slurry of 2.4 g. of glycoluril in 50 ml of water was heated to 60° C., adjusted to pH 9 by addition of dilute sodium hydroxide solution, and treated with 8.0 g. of 50% glutaraldehyde while maintaining the pH at 8–9. The resultant slurry was diluted with 50 ml additional water and filtered. Water was removed from the clear filtrate to give a white powder representing the product from 3 glutaraldehyde and 1 glycoluril. Anal. Found: N, 12.39%.

EXAMPLE III

Product from 2 glutaraldehyde: 1 5,5-dimethylhydantoin

A mixture of 1.34 g. of 5,5-dimethylhydantoin and 4.00 g. of 50% aqueous glutaraldehyde was diluted with 1.34 ml of water, treated with 0.2 ml of 10% aqueous sodium carbonate, and gently warmed with stirring. The suspension cleared, and the resulting solution was dried at 60° C. at reduced pressure to give the product as an off-white powder. Anal. Found: N, 7.70%.

EXAMPLE IV

Product from 1 glutaraldehyde: 1 5,5-dimethylhydantoin (a) A mixture of 134 g. (1.0 mole) of 5,5-dimethylhydantoin and 200 g. (1.0 mole) of 50% aqueous glutaraldehyde in 602 ml of water was stirred and adjusted to pH 8 by addition of 12.1 g. of 10% aqueous sodium hydroxide. The slurry was heated at 55° C. for 30 minutes, forming a clear yellow solution of the 1:1 reaction product.

(b) In another experiment, a granular solid was obtained after removal of water. Anal. Found: N, 13.99%.

EXAMPLE V

Product from 2 glutaraldehyde: 1 urea

A mixture of 6.0 g (0.1 mole) of urea and 40.0 g. (0.2 mole) of 50% aqueous glutaraldehyde was made alkaline with ca 0.1 ml of 50% aqueous sodium hydroxide, stirred at room temperature to a complete solution, and allowed to stand overnight at room temperature. Removal of water left off-white powdery product. Anal. Found: N, 10.07%.

EXAMPLE VI

Product from 1 glutaraldehyde: 1 urea

A mixture of 6.0 g. (0.1 mole) of urea and 20.0 g. (0.1 mole) of 50% aqueous glutaraldehyde was made alkaline by addition of ca 0.1 ml of 50% aqueous sodium hydroxide, stirred at room temperature to a complete solution, and allowed to stand overnight at room temperature. Water was removed leaving off-white powdery product. Anal. Found: 17.53%.

EXAMPLE VII

Product from 1 glutaraldehyde: 2 urea

A mixture of 12.0 g. (0.2 mole) of urea and 20.0 g. (0.1 mole) of 50% aqueous glutaraldehyde was made alkaline by addition of ca 0.1 ml of 50% aqueous sodium hydroxide, stirred at room temperature to a complete solution, and allowed to stand overnight at room temperature. A sample of solution was dried at reduced pressure, leaving product as an off-white powder. Anal. Found: N, 26.54%.

EXAMPLE VIII

The test procedure used to determine anti-microbial activity was a modification of a phenol coefficient procedure in common usage [Ref: "Official Methods of Analysis", 12th Edition, Association of Official Analytical Chemists, Washington, D.C. 1975, pp. 57–65] and has been described in detail previously [Ref: Berke and Rosen, J. Soc. Cosmet. Chem. 29, 757 (1978)]. In general, an inoculum of approximately $10^6$ microorganisms per ml. was added to a dilute test solution of nitrogen compound-glutaraldehyde product, and the mixture was incubated at 35° C. in the case of bacteria (P. aeruginosa) or yeast (C. albicans). Samples were taken from the incubated test solution after 3 days and subcultured into AOAC letheen Broth to determine if any of the microorganisms survived. The following table lists results of subcultures on tests carried out on some of the above-described nitrogen compound glutaraldehyde products. Growth in the subculture (+) indicates survival of some microorganisms, whereas no growth in the subculture (0) indicates the absence (or less than 10 organisms/ml) of microorganisms in the test solution.

| Product from Example | Glutaraldehyde-dimethylhydantoin Ratio | Concentration of Product | C. Albicans (ATCC 10231) 3-day Subculture |
|---|---|---|---|
| III | 2:1 | 0.2% | 0 |
| III | 2:1 | 0.1% | 0 |

| Product from Example | Glutaraldehyde-urea Ratio | Concentration of Product | P. Aeruginosa (ATCC 9027) 3-day Subculture |
|---|---|---|---|
| V | 2:1 | 0.5% | 0 |
| VI | 1:1 | 0.5% | 0 |
| VII | 1:2 | 0.5% | 0 |

EXAMPLE IX

Product from 1 glutaraldehyde: 1 formamide

A mixture of 8.16 g. (40.8 millimoles) of 50% aqueous glutaraldehyde and 1.84 g. (40.8 millimoles) of formamide was brough to pH 10–11 by addition of a catalytic amount of sodium hydroxide solution, and the yellow solution was stirred at room temperature overnight. Water was removed at reduced pressure, leaving 5.60 g. (95% yield) of dark yellow condensation product as a thick oil. Anal. Calcd. for $C_6H_{11}O_3N$ (145.17): N, 9.65. Found: N, 9.40.

EXAMPLE X

Product from 1 glutaraldehyde: 2 formamide

A mixture of 6.90 g. (34.4 millimoles) of 50% aqueous glutaraldehyde and 3.10 g. (68.8 millimoles) of formamide was adjusted to pH 11 by addition of a catalytic amount of sodium hydroxide solution, and the yellow solution was stirred at room temperature overnight. Water was removed at reduced pressure, leaving 7.05 g. (98% yield) of dark yellow condensation product as a thick oil. Anal. Calcd. for $C_7H_{14}O_4N \cdot H_2O$ (208.23): N, 13.45%. Found: N, 12.96%.

EXAMPLE XI

Product from 1 glutaraldehyde: 1 acetamide

A mixture of 7.72 g. (38.6 millimoles) of 50% aqueous glutaraldehyde and 2.28 g. (38.6 millimoles) of acetamide was brought to pH 11–12 by addition of a catalytic amount of sodium hydroxide solution, and the yellow solution was stirred for one hour and then allowed to stand overnight at room temperature. Water was removed at reduced pressure, leaving 6.62 g. of yellow condensation product as a thick oil. Anal. Calcd. for $C_7H_{13}O_3N$ (159.20): N, 8.80. Found: N, 8.75.

EXAMPLE XII

Product from 1 glutaraldehyde: 2 acetamide

A mixture of 6.29 g. (31.4 millimoles) of 50% aqueous glutaraldehyde and 3.71 g. (62.8 millimoles) of acetamide was stirred and brought to pH 11–12 by addition of a catalytic amount of sodium hydroxide solution. After being stirred for one hour, the yellow was allowed to stand at room temperature overnight. Water was removed at reduced pressure, leaving 6.23 g. of yellow condensation product as a thick oil. Anal. Calcd. for $C_9H_{18}O_4N_2$ (236.29): N, 11.86%. Found: N, 12.03%.

While the invention has now been described in terms of certain preferred embodiments, the skilled artisan will readily appreciate that various modifications, changes, omissions and substitutions may be made without departing from the spirit thereof. It is intended, therefore, that the present invention be limited solely by the scope of the following claims.

We claim:

1. A method for inhibiting microbial growth in a substance requiring microbial inhibition, comprising incorporating into said substance an effective microbial growth inhibiting amount of a reaction product of glutaraldehyde and a nitrogen-containing compound having the structural formula

where R and $R^1$ together with —NH—CO— to which they are attached form a cyclic amide or imide in the ratio of glutaraldehyde to nitrogen-containing compound between 1:2 and 4:1, with the proviso that said nitrogen-containing compound is not allantoin.

2. The method of claim 1, wherein said reaction product is the result of the reaction of glutaraldehyde and dimethylhydantoin in a molar ratio of glutaraldehyde to dimethylhydantoin in the range of about 1:1 to about 2:1.

3. The method of claim 2, wherein said reaction product is the result of a reaction between glutaraldehyde and dimethylhydantoin in the presence of a basic catalyst.

4. The method of claim 1, wherein said reaction product is the result of the reaction of glutaraldehyde and glycoluril in a molar ratio of glutaraldehyde to glycoluril in the range of about 1:1 to about 4:1.

5. The method of claim 4, wherein said reaction product is the result of a reaction between glutaraldehyde and glycoluril in the presence of a basic catalyst.

6. The method of claim 1, wherein said reaction product is the result of the reaction of glutaraldehyde and urea in a molar ratio of glutaraldehyde to urea in the range of about 2:1 to about 1:2.

7. The method of claim 6, wherein said reaction product is the result of a reaction between glutaraldehyde and urea in the presence of a basic catalyst.

8. The method of claim 1, wherein said reaction product is incorporated into said substance in an amount up to about 0.5% by weight, based upon the weight of said substance.

9. The method of claim 1, wherein said substance is a cosmetic product.

* * * * *